(12) United States Patent
Yuzawa

(10) Patent No.: US 12,033,248 B2
(45) Date of Patent: Jul. 9, 2024

(54) CORRECTION INSTRUCTION REGION DISPLAY APPARATUS, CORRECTION INSTRUCTION REGION DISPLAY METHOD, AND CORRECTION INSTRUCTION REGION DISPLAY PROGRAM

(71) Applicant: FUJIFILM Corporation, Tokyo (JP)

(72) Inventor: Takuya Yuzawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 431 days.

(21) Appl. No.: 17/525,942

(22) Filed: Nov. 14, 2021

(65) Prior Publication Data

US 2022/0076462 A1    Mar. 10, 2022

Related U.S. Application Data

(63) Continuation of application No. PCT/JP2020/018394, filed on May 1, 2020.

(30) Foreign Application Priority Data

Jun. 4, 2019    (JP) ................................. 2019-104701

(51) Int. Cl.
    *G06T 11/00*      (2006.01)
    *A61B 6/03*      (2006.01)
    (Continued)

(52) U.S. Cl.
    CPC ............ *G06T 11/008* (2013.01); *A61B 6/032* (2013.01); *A61B 6/463* (2013.01); *A61B 6/466* (2013.01);
    (Continued)

(58) Field of Classification Search
    CPC ..... G06T 7/11; G06T 11/008; G06T 2200/24; G06T 2207/10081; G06T 2207/10088;
    (Continued)

(56) References Cited

U.S. PATENT DOCUMENTS 8,351,670 B2    1/2013    Ijiri et al.
2008/0267481 A1*   10/2008    Nakamura ........... G06V 10/987
                                                           382/131

(Continued)

FOREIGN PATENT DOCUMENTS

| JP | H1057371 | 3/1998 |
|----|----------|--------|
| JP | 2009106426 | 5/2009 |
| JP | 2012014360 | 1/2012 |

OTHER PUBLICATIONS

"International Search Report (Form PCT/ISA/210) of PCT/JP2020/018394," mailed on Jun. 30, 2020, with English translation thereof, pp. 1-5.

(Continued)

*Primary Examiner* — Nay A Maung
*Assistant Examiner* — Jose M Torres
(74) *Attorney, Agent, or Firm* — JCIPRNET

(57) ABSTRACT

A first display control unit displays a first tomographic image of a three-dimensional image consisting of a plurality of tomographic images on a display unit, and superimposes and displays, as a first cross-section correction instruction region, a cross-section of a three-dimensional correction instruction region on the first tomographic image, which is used to correct a boundary of a region of interest extracted from the three-dimensional image, on the first tomographic image. A second display control unit displays at least one second tomographic image adjacent to the first tomographic image, which includes the three-dimensional correction instruction region, on the display unit, and superimposes and displays, as a second cross-section correction instruction region, a cross-section of the three-dimensional correction instruction region on the second tomographic image, on the second tomographic image.

10 Claims, 7 Drawing Sheets

(51) Int. Cl.
*A61B 6/46* (2024.01)
*G06T 7/11* (2017.01)
*G06V 10/22* (2022.01)
*G06V 10/25* (2022.01)

(52) U.S. Cl.
CPC .............. *G06T 7/11* (2017.01); *G06V 10/22* (2022.01); *G06V 10/25* (2022.01); *G06T 2207/10081* (2013.01); *G06T 2207/10088* (2013.01); *G06T 2207/20104* (2013.01); *G06T 2207/30004* (2013.01); *G06V 2201/031* (2022.01)

(58) Field of Classification Search
CPC . G06T 2207/20081; G06T 2207/20084; G06T 2207/20104; G06T 2207/30004; A61B 5/055; A61B 6/032; A61B 6/463; A61B 6/466; G06V 10/22; G06V 10/25; G06V 10/82; G06V 2201/031; G01T 1/161
See application file for complete search history.

(56) References Cited

U.S. PATENT DOCUMENTS

| | | | |
|---|---|---|---|
| 2009/0257550 A1* | 10/2009 | Moriya | G06T 19/00 378/4 |
| 2014/0286551 A1* | 9/2014 | Yoshida | G06T 7/0012 382/128 |
| 2016/0026266 A1 | 1/2016 | Douglas et al. | |
| 2018/0353078 A1* | 12/2018 | Lee | A61B 5/0073 |
| 2019/0139223 A1 | 5/2019 | Nie et al. | |
| 2021/0241016 A1* | 8/2021 | Hashimoto | A61B 5/055 |
| 2021/0256741 A1* | 8/2021 | Sakuragi | A61B 6/037 |

OTHER PUBLICATIONS

"Written Opinion of the International Searching Authority (Form PCT/ISA/237)" of PCT/JP2020/018394, mailed on Jun. 30, 2020, with English translation thereof, pp. 1-8.

* cited by examiner

CORRECTION INSTRUCTION REGION DISPLAY APPARATUS, CORRECTION INSTRUCTION REGION DISPLAY METHOD, AND CORRECTION INSTRUCTION REGION DISPLAY PROGRAM

CROSS-REFERENCE TO RELATED APPLICATIONS

This application is a Continuation of PCT International Application No. PCT/JP2020/018394 filed on May 1, 2020, which claims priority under 35 U.S.C § 119(a) to Japanese Patent Application No. 2019-104701 filed on Jun. 4, 2019. Each of the above application(s) is hereby expressly incorporated by reference, in its entirety, into the present application.

BACKGROUND OF THE INVENTION

1. Field of the Invention

The present disclosure relates to a correction instruction region display apparatus, a correction instruction region display method, and a non-transitory computer readable recording medium storing a correction instruction region display program that display a correction instruction region that is used to correct a boundary of a region of interest extracted in a three-dimensional image.

2. Description of the Related Art

In recent years, advances in medical equipment, such as a computed tomography (CT) apparatus and a magnetic resonance imaging (MRI) apparatus, have made it possible to perform diagnostic imaging using a higher quality three-dimensional image having higher resolution. A region of interest such as an organ and a lesion included in such a three-dimensional image has also been automatically extracted. However, in a case where the region of interest is automatically extracted, over-extraction and under-extraction may occur. In such a case, it is necessary to correct the boundary of the automatically extracted region of interest.

As a method of correcting the boundary, a method has been performed in which a two-dimensional tomographic image constituting a three-dimensional image is displayed, a cursor having a predetermined shape, such as a circle, is moved on the displayed tomographic image, and the over-extracted area is deleted from or the under-extracted area is added to the region of interest. However, in a case where the boundary of the region of interest is corrected for each tomographic image, the boundaries of the regions of interest in the cross-section perpendicular to the tomographic image may not be smoothly connected to each other.

In such a case, it is conceivable to three-dimensionally correct the boundary of the region of interest in the three-dimensional image by using a spherical three-dimensional cursor. However, in the cross-section perpendicular to the tomographic image, the boundary of the region of interest may not be spherical. Therefore, in a case where the boundary of the region of interest is corrected by using a spherical cursor, unintended over-correction or under-correction (hereinafter, referred to as over-correction or the like) may occur.

Meanwhile, a method has been proposed in which regions of interest are set in two tomographic images among a plurality of tomographic images constituting a three-dimensional image, the regions of interest set in the two tomographic images are interpolated into tomographic images that exist between the two tomographic images, and the region of interest is set (JP1998-57371A (JP-H10-57371A)). In addition, a method has also been proposed in which in response to deformation operation of a contour line of a region of interest in a designated tomographic plane, for a tomographic image constituting a three-dimensional image, deformation operation of the contour line in the other tomographic plane is performed (JP2012-14360A). The methods described in JP1998-57371A (JP-H10-57371A) and JP2012-14360A are used, so that the region of interest can be corrected even for a tomographic image that is not displayed.

SUMMARY OF THE INVENTION

However, in the method described in JP1998-57371A (JP-H10-57371A), a user does not know how the regions of interest are set in the tomographic images that exist between the two tomographic images until the set regions of interest are displayed. Further, in the method described in JP2012-14360A, the user also does not know how the contour line is deformed in the other tomographic plane until the other tomographic plane is displayed. For this reason, in the methods described in JP1998-57371A (JP-H10-57371A) and JP2012-14360A, unintended over-correction or the like in the region of interest may also occur.

The present disclosure has been made in view of the above circumstances, and an object thereof is to prevent, in a case where a region of interest for a tomographic image of one tomographic plane of a three-dimensional image is corrected, the occurrence of unintended over-correction or the like in a tomographic image of the other tomographic plane.

A correction instruction region display apparatus according to the present disclosure comprises: a first display control unit that displays a first tomographic image of a three-dimensional image consisting of a plurality of tomographic images on a display unit, and superimposes and displays, as a first cross-section correction instruction region, a cross-section of a three-dimensional correction instruction region on the first tomographic image, which is used to correct a boundary of a region of interest extracted from the three-dimensional image, on the first tomographic image; and a second display control unit that displays at least one second tomographic image adjacent to the first tomographic image, which includes the three-dimensional correction instruction region, on the display unit, and superimposes and displays, as a second cross-section correction instruction region, a cross-section of the three-dimensional correction instruction region on the second tomographic image, on the second tomographic image.

In the correction instruction region display apparatus according to the present disclosure, the second display control unit may display the second tomographic image and the second cross-section correction instruction region on the display unit, on the basis of a display instruction of the second tomographic image.

Further, in the correction instruction region display apparatus according to the present disclosure, the second display control unit may display a predetermined number of second tomographic images among a plurality of second tomographic images which include the three-dimensional correction instruction region, on the display unit.

Further, in the correction instruction region display apparatus according to the present disclosure, the second display control unit may display a partial region including the second cross-section correction instruction region in the second tomographic image, on the display unit.

Further, in the correction instruction region display apparatus according to the present disclosure, a first correction unit that corrects the boundary of the region of interest included in the first tomographic image in response to a correction instruction using the first cross-section correction instruction region for the boundary of the region of interest included in the first tomographic image may further be provided.

Further, in the correction instruction region display apparatus according to the present disclosure, a second correction unit that corrects the boundary of the region of interest included in the second tomographic image by using the second cross-section correction instruction region, in response to the correction instruction using the first cross-section correction instruction region for the boundary of the region of interest included in the first tomographic image may further be provided.

Further, in the correction instruction region display apparatus according to the present disclosure, the three-dimensional correction instruction region may be spherical.

Further, in the correction instruction region display apparatus according to the present disclosure, a region-of-interest extraction unit that extracts a region of interest from each of the plurality of tomographic images may further be provided.

A correction instruction region display method according to the present disclosure comprises: displaying a first tomographic image of a three-dimensional image consisting of a plurality of tomographic images on a display unit, and superimposing and displaying, as a first cross-section correction instruction region, a cross-section of a three-dimensional correction instruction region on the first tomographic image, which is used to correct a boundary of a region of interest extracted from the three-dimensional image, on the first tomographic image; and displaying at least one second tomographic image adjacent to the first tomographic image, which includes the three-dimensional correction instruction region, on the display unit, and superimposing and displaying, as a second cross-section correction instruction region, a cross-section of the three-dimensional correction instruction region on the second tomographic image, on the second tomographic image.

The correction instruction region display method according to the present disclosure may also be provided as a non-transitory computer readable recording medium storing a program to be executed by a computer.

Another correction instruction region display apparatus according to the present disclosure comprises: a memory that stores a command to be executed by a computer; and a processor configured to execute the stored command, in which the processor executes processing of displaying a first tomographic image of a three-dimensional image consisting of a plurality of tomographic images on a display unit, and superimposing and displaying, as a first cross-section correction instruction region, a cross-section of a three-dimensional correction instruction region on the first tomographic image, which is used to correct a boundary of a region of interest extracted from the three-dimensional image, on the first tomographic image, and displaying at least one second tomographic image adjacent to the first tomographic image, which includes the three-dimensional correction instruction region, on the display unit, and superimposing and displaying, as a second cross-section correction instruction region, a cross-section of the three-dimensional correction instruction region on the second tomographic image, on the second tomographic image.

According to the present disclosure, in a case where a region of interest for a tomographic image of one tomographic plane of a three-dimensional image is corrected, the occurrence of unintended over-correction or the like in a tomographic image of the other tomographic plane can be prevented.

DESCRIPTION OF THE PREFERRED EMBODIMENTS

Figure 1:
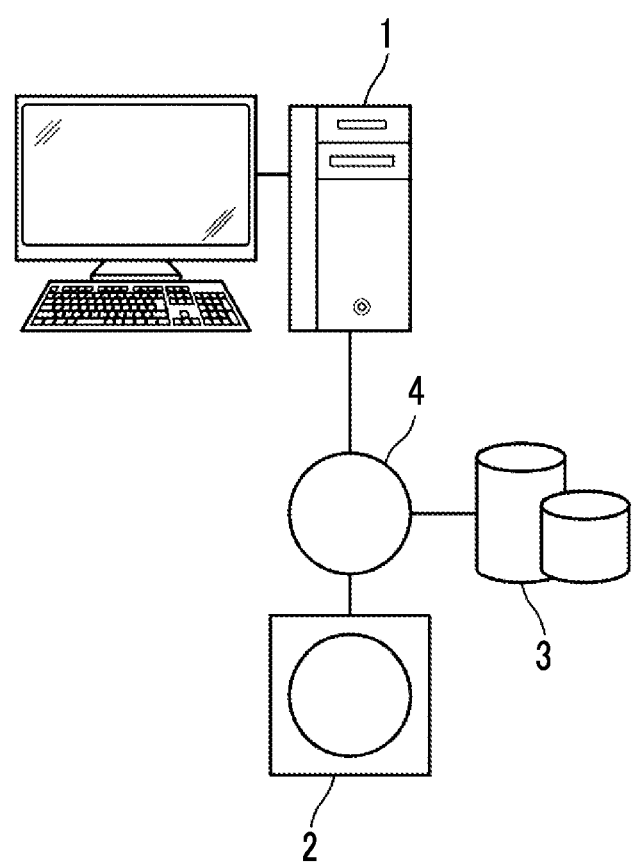
FIG. 1 is a hardware configuration diagram showing an outline of a diagnosis support system to which a correction instruction region display apparatus according to an embodiment of the present disclosure is applied.

Hereinafter, an embodiment of the present disclosure will be described with reference to the drawings. FIG. 1 is a hardware configuration diagram showing an outline of a diagnosis support system to which a correction instruction region display apparatus according to the embodiment of the present disclosure is applied. As shown in FIG. 1, in the diagnosis support system, a correction instruction region display apparatus 1, a three-dimensional image capturing apparatus 2, and an image storage server 3 according to the present embodiment are connected to communicate with one another via a network 4.

The three-dimensional image capturing apparatus 2 is an apparatus that images an area to be diagnosed of a subject and that generates a three-dimensional image representing the area, and specific examples thereof include a CT apparatus, an MRI apparatus, and a positron emission tomography (PET) apparatus. The three-dimensional image generated by the three-dimensional image capturing apparatus 2 is transmitted to and stored in the image storage server 3. In the present embodiment, the three-dimensional image capturing apparatus 2 is a CT apparatus and generates a CT image including the area to be diagnosed of the subject, as a three-dimensional image G0. In addition, the three-dimensional image G0 consists of a plurality of tomographic images.

The image storage server 3 is a computer that stores and manages various data and comprises a large-capacity external storage device and database management software. The image storage server 3 communicates with another apparatus via a wired or wireless network 4 to transmit and receive image data and the like. Specifically, the image storage server 3 acquires various data including the image data of the three-dimensional image G0 generated by the three-dimensional image capturing apparatus 2 via the network, and stores and manages the acquired data on a recording medium such as a large-capacity external storage device. A storage format of the image data and the communication between the apparatuses via the network 4 are based on a protocol such as digital imaging and communications in medicine (DICOM).

The correction instruction region display apparatus 1 is an apparatus obtained by installing a correction instruction region display program of the present embodiment on one computer. The computer may be a workstation or a personal computer directly operated by a doctor who makes diagnosis, or may be a server computer connected to the workstation or the personal computer via a network 4. The correction instruction region display program is stored on a storage device of a server computer connected to the network 4 or on network storage so as to be accessible from the outside, and is downloaded and installed on a computer that the doctor uses according to a request. Alternatively, the correction instruction region display program is recorded on a recording medium, such as a digital versatile disc (DVD) or a compact disc read only memory (CD-ROM), and is distributed and installed on a computer from the recording medium.

Figure 2:
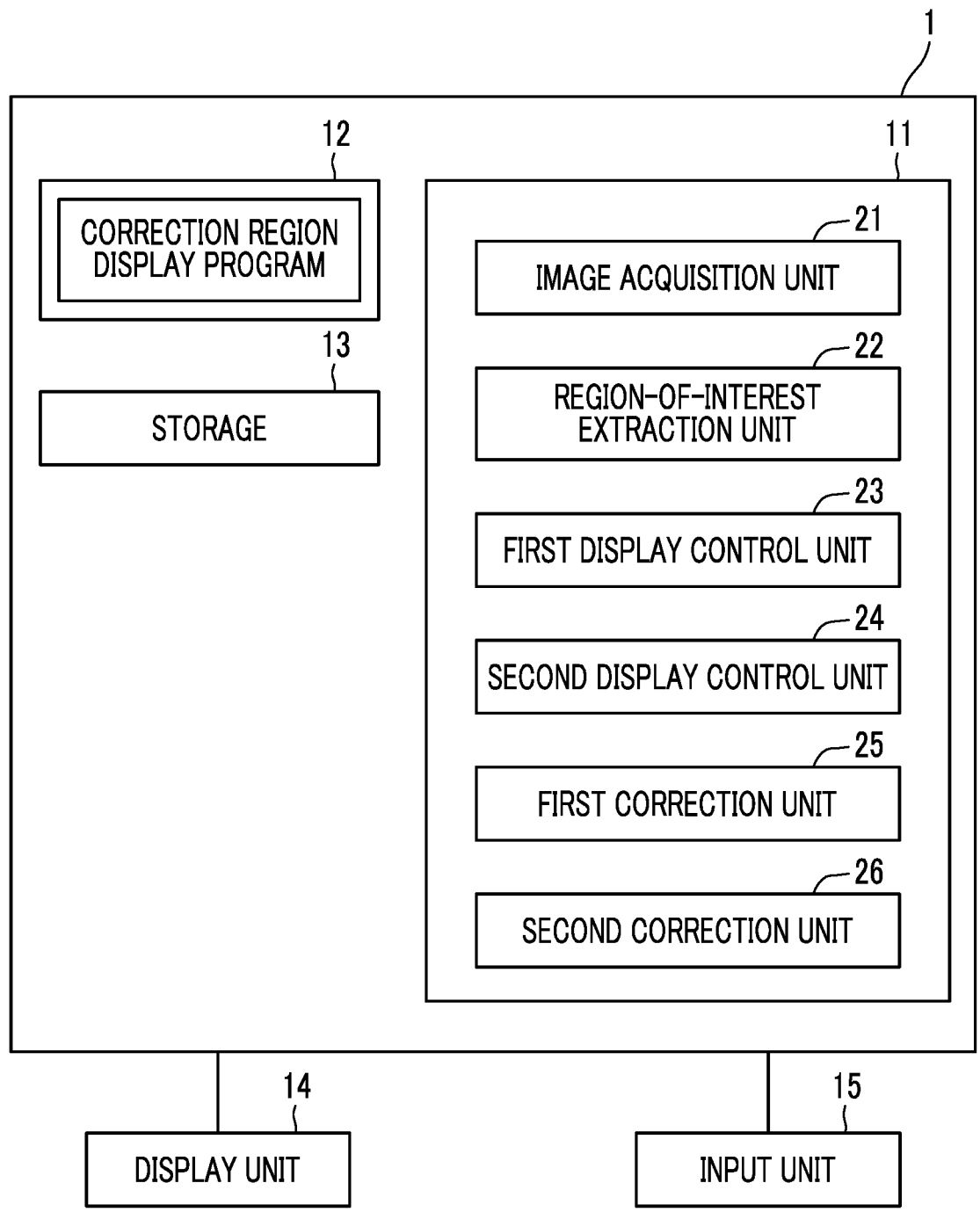
FIG. 2 is a diagram showing a schematic configuration of the correction instruction region display apparatus according to the embodiment of the present disclosure.

FIG. 2 is a diagram showing the schematic configuration of the correction instruction region display apparatus that is realized with the correction instruction region display program installed on a computer. As shown in FIG. 2, the correction instruction region display apparatus 1 comprises a central processing unit (CPU) 11, a memory 12, and a storage 13, as a standard workstation configuration. Further, a display unit 14, such as a liquid crystal display, and an input unit 15, such as a keyboard and a mouse, are connected to the correction instruction region display apparatus 1.

The storage 13 includes a hard disk drive or the like, and stores the three-dimensional image G0 acquired from the image storage server 3 via the network 4 and various information including information necessary for processing.

Further, the correction instruction region display program is stored in the memory 12. The correction instruction region display program defines the following processing as a process to be executed by the CPU 11: image acquiring processing of acquiring a three-dimensional image G0; region-of-interest extracting processing of extracting a region of interest from each of the plurality of tomographic images constituting the three-dimensional image G0; first display controlling processing of displaying a first tomographic image of the plurality of tomographic images on a display unit 14, and superimposing and displaying, as a first cross-section correction instruction region, a cross-section of a three-dimensional correction instruction region on the first tomographic image, which is used to correct a boundary of the region of interest extracted from the three-dimensional image G0, on the first tomographic image; second display controlling processing of displaying at least one second tomographic image adjacent to the first tomographic image, which includes the three-dimensional correction instruction region, on the display unit 14, and superimposing and displaying, as a second cross-section correction instruction region, a cross-section of the three-dimensional correction instruction region on the second tomographic image, on the second tomographic image; first correcting processing of correcting the boundary of the region of interest included in the first tomographic image in response to a correction instruction using the first cross-section correction instruction region for the boundary of the region of interest included in the first tomographic image; and second correcting processing of correcting the boundary of the region of interest included in the second tomographic image by using the second cross-section correction instruction region, in response to the correction instruction using the first cross-section correction instruction region for the boundary of the region of interest included in the first tomographic image.

The CPU 11 executes the processing according to the program to make a computer function as an image acquisition unit 21, a region-of-interest extraction unit 22, a first display control unit 23, a second display control unit 24, a first correction unit 25, and a second correction unit 26.

The image acquisition unit 21 acquires the three-dimensional image G0 including the region of interest, from the image storage server 3 via an interface (not shown) connected to the network 4. The region of interest is an organ, a specific region within the organ, or a region of a structure, such as bone and cartilage, that the user is interested in, for example, as a diagnosis target. In a case where the three-dimensional image G0 is already stored in the storage 13, the image acquisition unit 21 may acquire the three-dimensional image G0 from the storage 13.

The region-of-interest extraction unit 22 extracts the region of interest from the three-dimensional image G0. For the extraction, the region-of-interest extraction unit 22 comprises a learned model that has performed machine learning so as to extract the region of interest from the three-dimensional image G0. The learned model includes a neural network that has performed deep learning so as to extract, as a region of interest, an organ, a specific region within the organ, or a region of a structure, such as bone and cartilage, which is a diagnosis target. Examples of the organ as a diagnosis target include a heart, liver, lungs, kidneys, and brain. In the present embodiment, for example, white matter of the brain is the region of interest. In a case where the input of the three-dimensional image G0 is received, the learned model outputs a determination result indicating whether or not each pixel of the three-dimensional image G0 corresponds to the region of interest. The region-of-interest extraction unit 22 extracts a region consisting of pixels determined to correspond to the region of interest, as the region of interest.

In addition to the neural network that has performed deep learning, the learned model may include, for example, a support vector machine (SVM), a convolutional neural network (CNN), and a recurrent neural network (RNN). Further, the region-of-interest extraction unit 22 is not limited to a unit provided with the learned model that has performed machine learning. For example, the region of interest may be extracted by template matching, threshold value processing, or the like.

Figure 3:
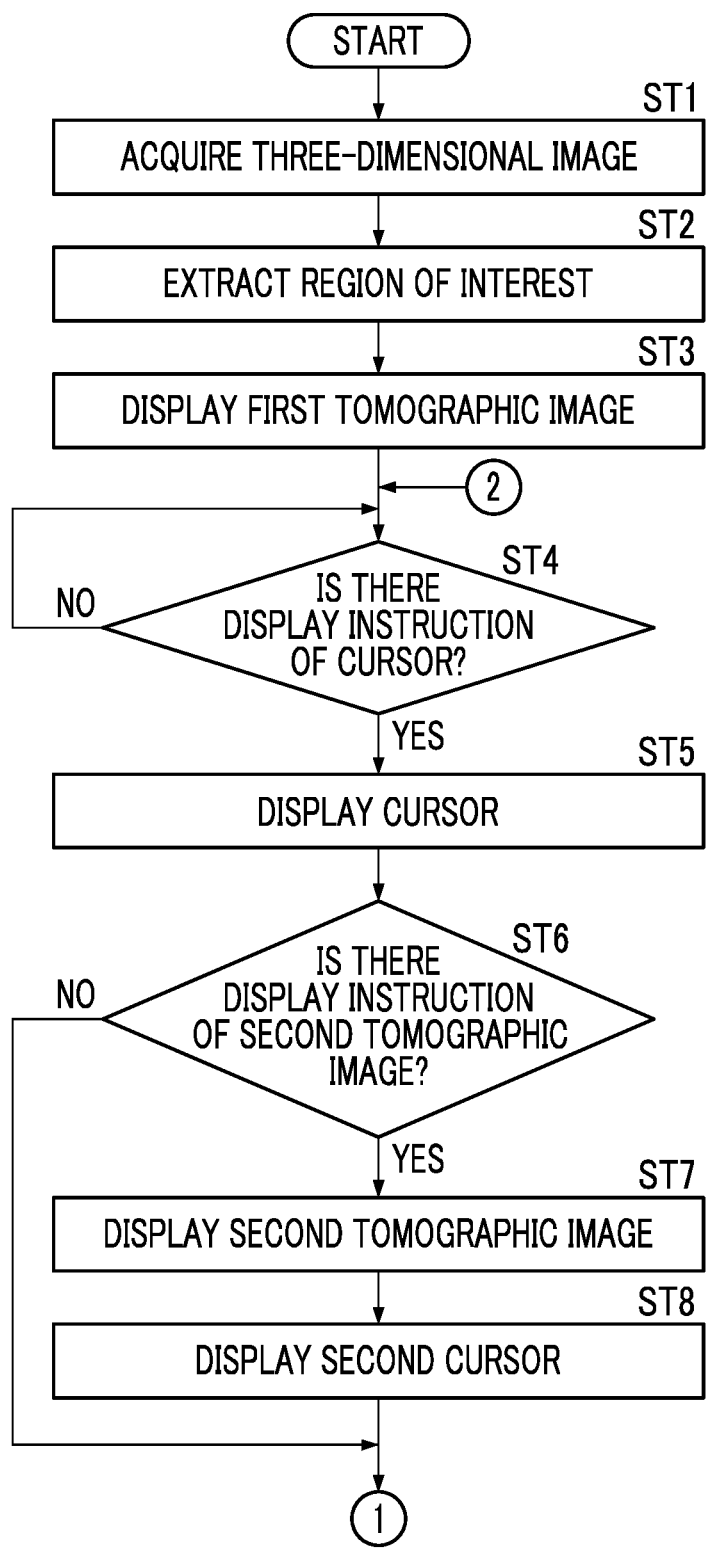
FIG. 3 is a flowchart showing processing performed in the present embodiment.
Figure 4:
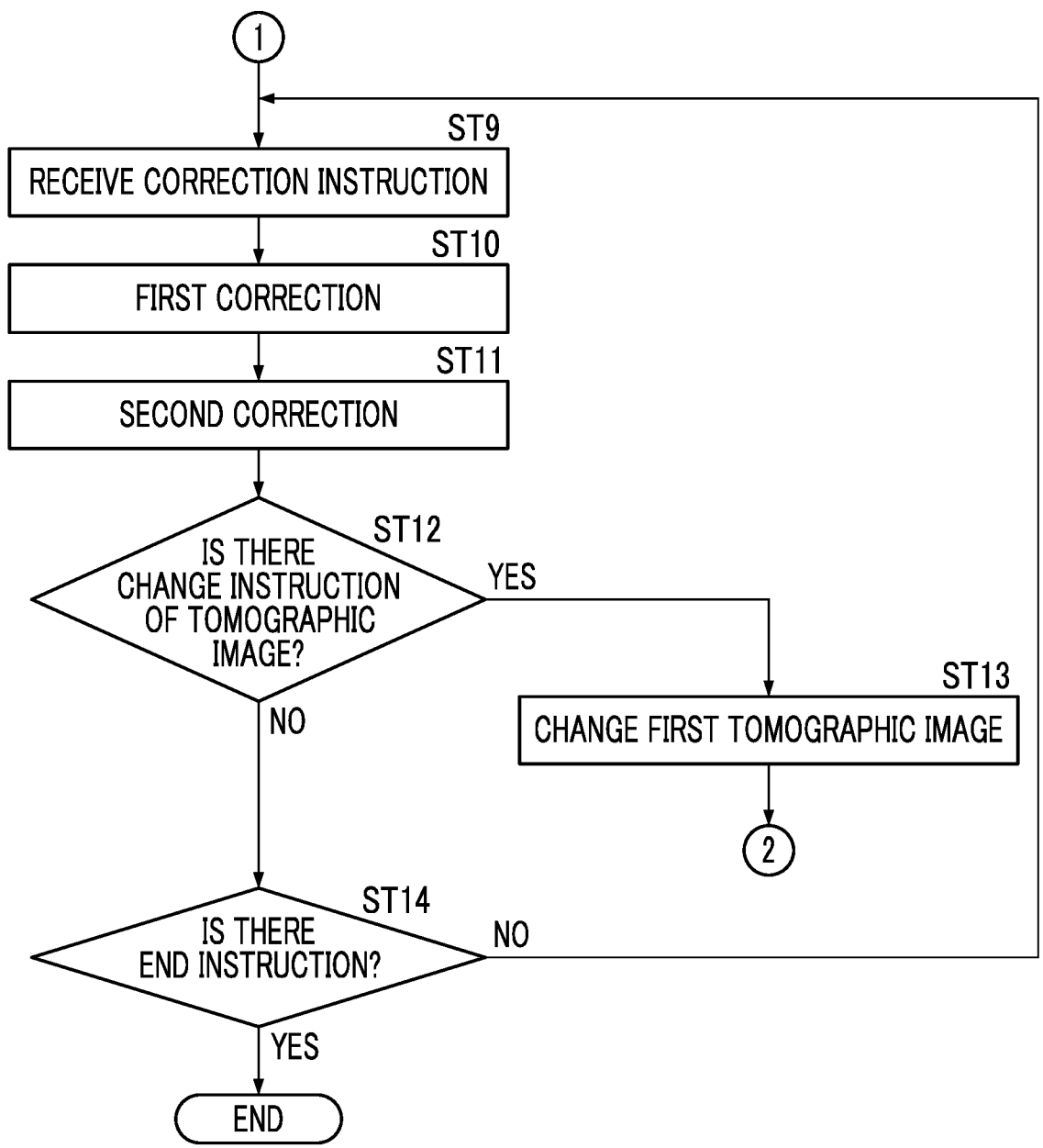
FIG. 4 is a flowchart showing processing performed in the present embodiment.

Hereinafter, processing performed by the first display control unit 23, the second display control unit 24, the first correction unit 25, and the second correction unit 26 will be described. FIGS. 3 and 4 are flowcharts showing processing performed in the present embodiment. First, the image acquisition unit 21 acquires a three-dimensional image G0 (Step ST1). Next, the region-of-interest extraction unit 22 extracts a region of interest from the three-dimensional image G0 (Step ST2). The first display control unit 23 displays a first tomographic image Dk, as a correction target of the region of interest, among the plurality of tomographic images Dj (j=1 to n, n is the number of tomographic images) constituting the three-dimensional image G0, on the display unit 14 (Step ST3). The first tomographic image Dk to be displayed may be a tomographic image having any cross-section of an axial cross-section, a sagittal cross-section, or a coronal cross-section.

Figure 5:
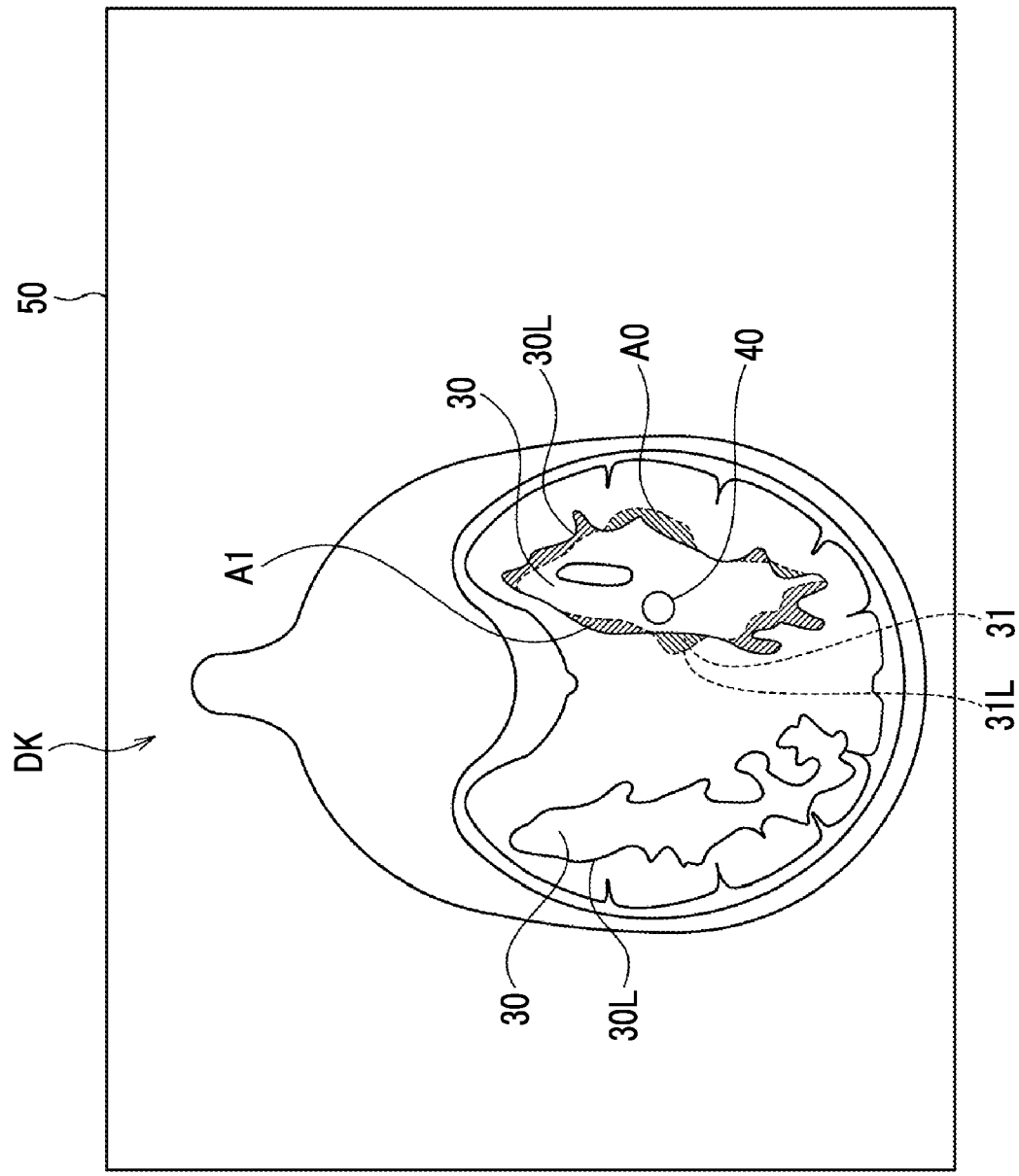
FIG. 5 is a diagram showing a display screen of a first tomographic image.

FIG. 5 is a diagram showing a display screen of the first tomographic image Dk. As shown in FIG. 5, the first tomographic image Dk included on a display screen 50 is an image of an axial cross-section of a head of a human body, and includes a boundary 30L of an extracted region of interest 30 (that is, white matter). The tomographic image Dk shown in FIG. 5 is a view of the brain from below the human body. The region of interest 30 is included in the first tomographic image Dk, as a mask. The mask may be a mask represented by only the outline of the region of interest 30, a mask in which the entire region of interest 30 is hatched, or a mask in which the entire region of interest 30 is colored in a predetermined color. In the following description, the region of interest 30 means a region masked because of the extraction from the first tomographic image Dk by the region-of-interest extraction unit 22.

Here, the extraction result by the region-of-interest extraction unit 22 may not be always accurate, and the region of interest 30 may not completely match with an actual region of interest 31 included in the first tomographic image Dk. FIG. 5 shows a boundary 31L of the actual region of interest 31 via a broken line. In such a case, as shown in FIG. 5, it is necessary to add an under-extracted region A0 to the region of interest 30 and to delete an over-extracted region A1 from the region of interest 30. Therefore, the user corrects the boundary 30L of the extracted region of interest 30 by using the input unit 15. Since the processing for the white matter of a left brain and a right brain is the same, in FIG. 5 and the following description, only the processing for the left brain will be described, and the processing for the right brain will be omitted.

Next, the first display control unit 23 starts monitoring whether or not a display instruction of a cursor is given through the input unit 15 (Step ST4). In a case where affirmative determination is made in Step ST4, the first display control unit 23 displays the first tomographic image Dk with the three-dimensional cursor superimposed thereon, on the display unit 14 (display the cursor; Step ST5). In a case where negative determination is made in Step ST4, monitoring whether or not the display instruction of the cursor is given through the input unit 15 is repeated (Step ST4). In the present embodiment, the three-dimensional cursor is spherical. For this reason, in the present embodiment, as shown in FIG. 5, a cross-section of the three-dimensional cursor on the first tomographic image Dk is displayed as a circular first cursor 40, on the display unit 14. In the present embodiment, the size of the three-dimensional cursor can be designated by the input of the radius or diameter of the three-dimensional cursor through the input unit 15. Further, the three-dimensional cursor corresponds to the three-dimensional correction instruction region of the present disclosure, and the first cursor 40 corresponds to the first cross-section correction instruction region of the present disclosure.

Figure 6:
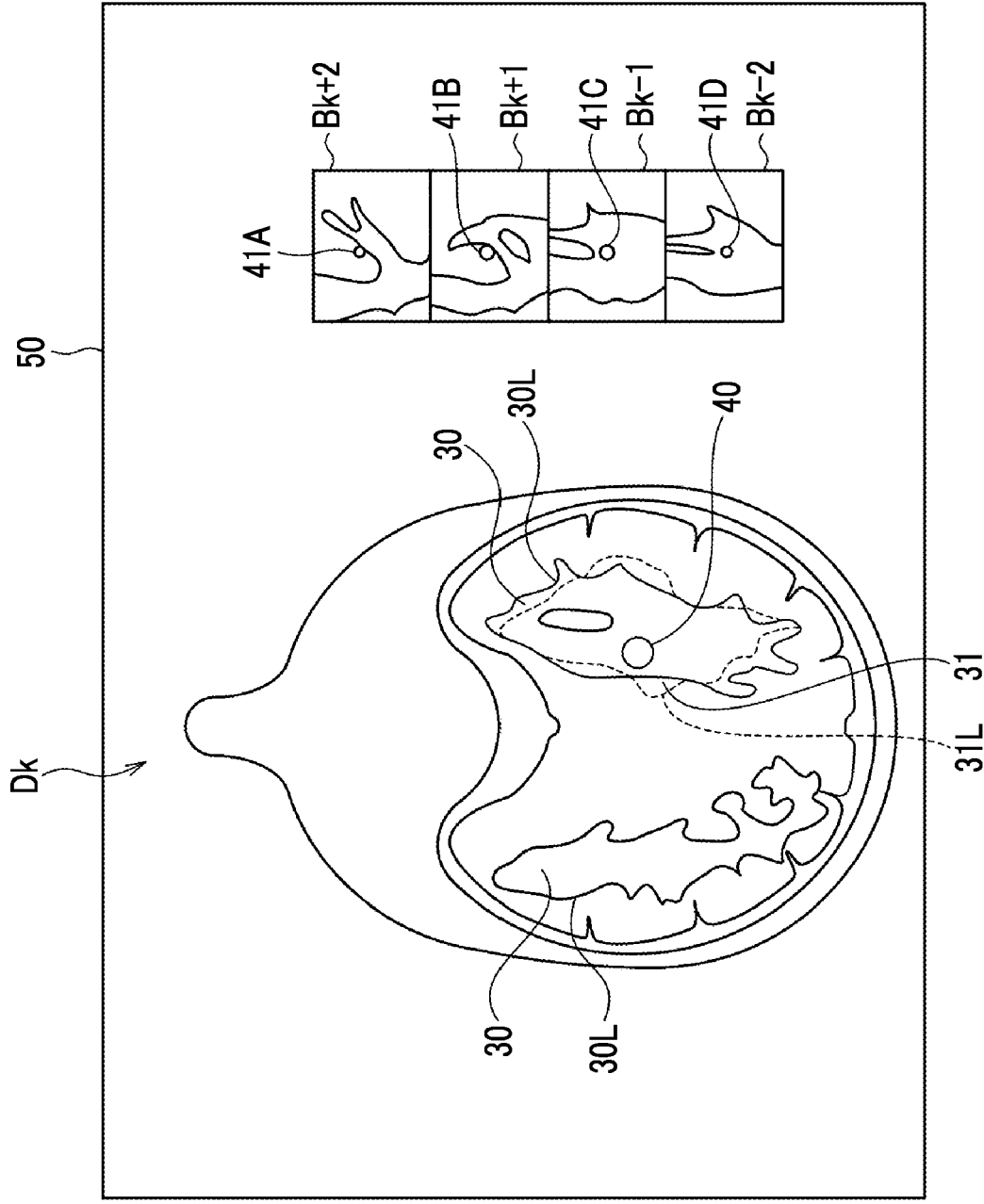
FIG. 6 is a diagram showing a state in which partial images of second tomographic images are displayed.

Subsequently, the second display control unit 24 determines whether or not a display instruction of the second tomographic image is given through the input unit 15 (Step ST6). In a case where affirmative determination is made in Step ST6, the second display control unit 24 displays a partial image of at least one second tomographic image adjacent to the first tomographic image, which includes the three-dimensional cursor, on the display unit 14 (display the second tomographic image; Step ST7). In a case where, for example, the input unit 15 has a keyboard, the display instruction of the second tomographic image can be given through the pressing of a control key on the keyboard, but the instruction is not limited thereto. Further, the second display control unit 24 superimposes and displays, as a second cursor, a cross-section of the three-dimensional cursor on the second tomographic image, on the partial image of the second tomographic image (Step ST8). FIG. 6 is a diagram showing a state in which the partial images of the second tomographic images are displayed on the display unit 14.

Figure 7:
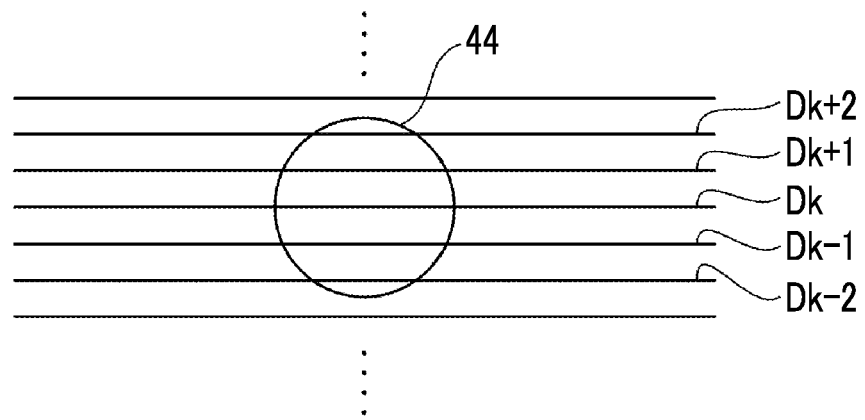
FIG. 7 is a diagram for explaining tomographic images including a three-dimensional cursor.

Here, since the three-dimensional cursor is spherical, as shown in FIG. 7, a plurality of second tomographic images Dk−2, Dk−1, Dk+1, and Dk+2 (here, two on each of the upper and lower sides) adjacent to the first tomographic image Dk are included in a three-dimensional cursor 44. Therefore, in the present embodiment, the second display control unit 24 displays partial images Bk−2, Bk−1, Bk+1, and Bk+2 of four second tomographic images Dk−2, Dk−1, Dk+1, and Dk+2 except the first tomographic image Dk, among five tomographic images in which the three-dimensional cursor 44 is included, on the display unit 14. The partial images Bk−2, Bk−1, Bk+1, and Bk+2 are regions having predetermined sizes and centered on cross sections of the three-dimensional cursor 44 included in the second tomographic images Dk−2, Dk−1, Dk+1, and Dk+2, respectively. Further, the sizes of the cross-sections of the three-dimensional cursor 44 included in the second tomographic images Dk−2, Dk−1, Dk+1, and Dk+2 differ from one another depending on the distance from the first tomographic image Dk. Therefore, circular second cursors 41A to 41D having sizes based on the distances from the first tomographic image Dk are superimposed and displayed on the partial images Bk+2, Bk+1, Bk−1, and Bk−2 of the second tomographic images displayed on the display unit 14, respectively. The second cursors 41A to 41D correspond to the second cross-section correction instruction regions of the present disclosure.

In a case where negative determination is made in Step ST6 or the process follows Step ST8, the first correction unit 25 receives a correction instruction using the three-dimensional cursor 44 by the user (Step ST9). In this case, the user moves the first cursor 40 by using the mouse of the input unit 15 to give the correction instruction so that the boundary 30L of the region of interest 30 matches with the boundary 31L of the actual region of interest 31. The first correction unit 25 corrects the boundary 30L of the region of interest 30 in the first tomographic image Dk by using the first cursor 40 in accordance with the correction instruction by the user (first correction; Step ST10). Further, the second correction unit 26 corrects the boundaries of the regions of interest included in the second tomographic images Dk+2, Dk+1, Dk−1, and Dk−2 by using the second cursors 41A to 41D, respectively, in response to the correction instruction of the boundary 30L of the region of interest 30 of the first tomographic image Dk (second correction; Step ST11).

Subsequently, determination is made whether or not a change instruction of the tomographic image to be corrected is input through the input unit 15 (Step ST12). In a case where affirmative determination is made in Step ST12, the first tomographic image displayed on the display unit 14 is changed (Step ST13), the process returns to Step ST4, and the processing after Step ST4 is repeated. In a case where negative determination is made in Step ST12, determination is made whether or not an end instruction is given (Step ST14). In a case where negative determination is made in Step ST14, the process returns to Step ST9, and the processing after Step ST9 is repeated. In a case where affirmative determination is made in Step ST14, the processing ends.

As described above, in the present embodiment, the first tomographic image Dk is displayed, and the cross-section of the three-dimensional cursor 44 on the first tomographic image Dk is superimposed and displayed on the first tomographic image Dk, as the first cursor 40. Further, the second tomographic images Dk−2, Dk−1, Dk+1, or Dk+2 adjacent to the first tomographic image Dk, in which the three-dimensional cursor 44 is included are displayed, and the cross-sections of the three-dimensional cursor 44 on the second tomographic images are superimposed and displayed as the second cursors 41A to 41D, on the second tomographic images Dk+2, Dk+1, Dk−1, and Dk−2, respectively. The second tomographic image arranged adjacent to the first tomographic image Dk may be at least one of the second tomographic images Dk−2, Dk−1, Dk+1, and Dk+2. Therefore, in a case where the boundary 30L of the region of interest 30 in the first tomographic image Dk is corrected by using the three-dimensional cursor 44, the user sees the displayed second tomographic images Dk−2, Dk−1, Dk+1, and Dk+2, so that the user can confirm how the region of interest is corrected by the three-dimensional cursor 44 in the second tomographic images Dk−2, Dk−1, Dk+1, and Dk+2 adjacent to the first tomographic image Dk. In addition, processing such as changing the size of the three-dimensional cursor 44 may be performed so that over-correction does not occur. Therefore, according to the present embodiment, in a case where a region of interest for a tomographic image of one tomographic plane of a three-dimensional image G0 is corrected, the occurrence of unintended over-correction or the like in a tomographic image of the other tomographic plane can be prevented.

Further, in the present embodiment, in a case where there is the display instruction of the second tomographic images Dk−2, Dk−1, Dk+1, and Dk+2, the second tomographic images Dk−2, Dk−1, Dk+1, and Dk+2 are displayed. Therefore, in a case where the boundary 30L of the region of interest 30 is corrected, the second tomographic images Dk−2, Dk−1, Dk+1, and Dk+2 are not displayed, so that resources such as the CPU 11 and the memory 12 are not consumed in order to display the second tomographic images Dk−2, Dk−1, Dk+1, and Dk+2. Accordingly, it is possible to prevent the correcting processing from becoming heavy as compared with a case where the second tomographic images Dk−2, Dk−1, Dk+1, and Dk+2 are always displayed. Further, since the partial images Bk−2, Bk−1, Bk+1, and Bk+2 of the second tomographic images Dk−2, Dk−1, Dk+1, and Dk+2 are displayed, the consumption of resources such as the CPU 11 and the memory 12 is reduced as compared with a case where the entire second tomographic images Dk−2, Dk−1, Dk+1, and Dk+2 are displayed. As a result, it is possible to prevent the processing for display from becoming heavy.

In the present embodiment, in a case where there is the display instruction of the second tomographic images Dk−2, Dk−1, Dk+1, and Dk+2, the second tomographic images Dk−2, Dk−1, Dk+1, and Dk+2 are displayed, but the present disclosure is not limited thereto. In a case where there is the display instruction of the first tomographic image Dk, the second tomographic images Dk−2, Dk−1, Dk+1, and Dk+2 may be displayed at the same time as the first tomographic image Dk.

Further, in the above-described embodiment, the partial images of the second tomographic images Dk−2, Dk−1, Dk+1, and Dk+2 are displayed, but the present disclosure is not limited thereto. The second tomographic images Dk−2, Dk−1, Dk+1, and Dk+2 may be displayed as they are on the display unit 14. In this case, the first tomographic image Dk and the second tomographic images Dk−2, Dk−1, Dk+1, and Dk+2 may be displayed side by side on the display unit 14, and the first tomographic image Dk and the second tomographic images Dk−2, Dk−1, Dk+1, and Dk+2 may be switched and displayed.

Further, in the above-described embodiment, partial images of the second tomographic images Dk−2, Dk−1, Dk+1, and Dk+2, two on each of the upper and lower sides of the first tomographic image Dk, are displayed, but the present disclosure is not limited thereto. Only the second tomographic images Dk−1 and Dk+1 on the upper and lower sides of the first tomographic image Dk, or only the second tomographic image, either one on the upper or lower side of the first tomographic image Dk, may be displayed.

Figure 8:
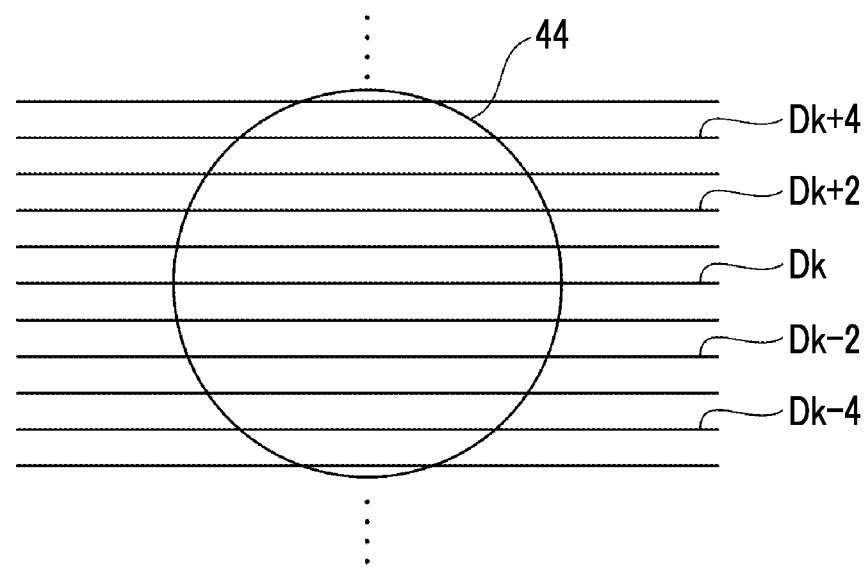
FIG. 8 is a diagram for explaining tomographic images including the three-dimensional cursor.

Further, in the above-described embodiment, in a case where the size of the three-dimensional cursor 44 is enlarged, more tomographic images are included in the three-dimensional cursor. For example, as shown in FIG. 8, in a case where the size of the three-dimensional cursor 44 is enlarged, five tomographic images on each of the upper and lower sides of the first tomographic image Dk are included in the three-dimensional cursor. In this case, ten second tomographic images or partial images thereof may be displayed on the display unit 14. However, the larger the number of second tomographic images to be displayed is, the heavier the processing for display is. Therefore, regardless of the number of tomographic images included in the three-dimensional cursor 44, the predetermined number of second tomographic images or partial images thereof may be displayed. For example, among the ten tomographic images shown in FIG. 8, the second tomographic images Dk−4, Dk−2, Dk+2, and Dk+4, two on each of the upper and lower sides, may be displayed on the display unit 14.

Further, in the above-described embodiment, the three-dimensional cursor is spherical, but the present disclosure is not limited thereto. A three-dimensional cursor having any shape, such as a rectangular parallelepiped, a cube, or a shape in which the bottom surfaces of two cones are connected to each other, may be used, as long as the three-dimensional cursor has a three-dimensional shape.

Further, in the above-described embodiment, the correction instruction region display apparatus 1 comprises the region-of-interest extraction unit 22, but the present disclosure is not limited thereto. The region of interest may be extracted by a separate apparatus connected to the correction instruction region display apparatus 1 via the network 4. Further, the three-dimensional image G0 to be acquired may be an image in which a region of interest is already extracted.

Further, in the above-described embodiment, for example, as a hardware structure of a processing unit that executes various processing such as processing performed by the image acquisition unit 21, the region-of-interest extraction unit 22, the first display control unit 23, the second display control unit 24, the first correction unit 25, and the second correction unit 26, the following various processors may be used. The various processors include, for example, a programmable logic device (PLD), such as a field programmable gate array (FPGA), which is a processor having a changeable circuit configuration after manufacture, and a dedicated electrical circuit, such as an application specific integrated circuit (ASIC), which is a processor having a dedicated circuit configuration designed to perform specific processing, in addition to the CPU which is a generalpurpose processor that executes software (programs) to function as various processing units as described above.

One processing unit may be constituted of one of the various processors or may be constituted of a combination of two or more processors of the same type or different types (for example, a combination of a plurality of FPGAs and a combination of a CPU and an FPGA).

Further, the plurality of processing units may constitute one processor.

A first example of the configuration in which the plurality of processing units are constituted of one processor is an aspect in which one or more CPUs and software are combined to constitute one processor and the processor functions as a plurality of processing units. A representative example of the aspect is a computer such as a client and server. A second example of the configuration is an aspect in which a processor that implements all of the functions of a system including the plurality of processing units with one integrated circuit (IC) chip is used. A representative example of the aspect is a system on chip (SoC). As described above, as the hardware structure of various processing units, one or more of the various processors are used.

Further, as the hardware structure of the various processors, more specifically, an electrical circuit (circuitry) in which circuit elements such as semiconductor elements are combined may be used.

EXPLANATION OF REFERENCES

1: correction instruction region display apparatus
2: three-dimensional image capturing apparatus
3: image storage server
4: network
11: CPU
12: memory
13: storage
14: display
15: input unit
21: image acquisition unit
22: region-of-interest extraction unit
23: first display control unit
24: second display control unit
25: first correction unit
26: second correction unit
30: region of interest
30L: boundary of region of interest
31: actual region of interest
31L: boundary of actual region of interest
40: first cursor
41A to 41D: second cursor
44: three-dimensional cursor
50: display screen
Dk: first tomographic image
Dk−2, Dk−1, Dk+1, Dk+2: second tomographic image
Bk−2, Bk−1, Bk+1, Bk+2: partial image of second tomographic image

What is claimed is:

1. A correction instruction region display apparatus comprising a processor,
wherein the processor is configured to:
control to display a first tomographic image of a three-dimensional image consisting of a plurality of tomographic images on a display unit, and superimpose and display, as a first cross-section correction instruction region, a cross-section of a three-dimensional correction instruction region on the first tomographic image, which is used to correct a boundary of a region of interest extracted from the three-dimensional image, on the first tomographic image; and
control to display at least one second tomographic image adjacent to the first tomographic image, which includes the three-dimensional correction instruction region, on the display unit, and superimpose and display, as a second cross-section correction instruction region, a cross-section of the three-dimensional correction instruction region on the second tomographic image, on the second tomographic image.

2. The correction instruction region display apparatus according to claim 1,
wherein the processor is configured to control to display the second tomographic image and the second cross-section correction instruction region on the display unit, on the basis of a display instruction of the second tomographic image.

3. The correction instruction region display apparatus according to claim 1,
wherein the processor is configured to control to display a predetermined number of second tomographic images among a plurality of second tomographic images which include the three-dimensional correction instruction region, on the display unit.

4. The correction instruction region display apparatus according to claim 1,
wherein the processor is configured to control to display a partial region including the second cross-section correction instruction region in the second tomographic image, on the display unit.

5. The correction instruction region display apparatus according to claim 1,
wherein the processor is further configured to correct the boundary of the region of interest included in the first tomographic image in response to a correction instruction using the first cross-section correction instruction region for the boundary of the region of interest included in the first tomographic image.

6. The correction instruction region display apparatus according to claim 5,
wherein the processor is further configured to correct the boundary of the region of interest included in the second tomographic image by using the second cross-section correction instruction region, in response to the correction instruction using the first cross-section correction instruction region for the boundary of the region of interest included in the first tomographic image.

7. The correction instruction region display apparatus according to claim 1,
wherein the three-dimensional correction instruction region is spherical.

8. The correction instruction region display apparatus according to claim 1,
wherein the processor is further configured to extract the region of interest from each of the plurality of tomographic images.

9. A correction instruction region display method comprising:
displaying a first tomographic image of a three-dimensional image consisting of a plurality of tomographic images on a display unit, and superimposing and displaying, as a first cross-section correction instruction region, a cross-section of a three-dimensional correction instruction region on the first tomographic image, which is used to correct a boundary of a region of interest extracted from the three-dimensional image, on the first tomographic image; and displaying at least one second tomographic image adjacent to the first tomographic image, which includes the three-dimensional correction instruction region, on the display unit, and superimposing and displaying, as a second cross-section correction instruction region, a cross-section of the three-dimensional correction instruction region on the second tomographic image, on the second tomographic image.

10. A non-transitory computer readable recording medium storing a correction instruction region display program causing a computer to execute a process comprising:

displaying a first tomographic image of a three-dimensional image consisting of a plurality of tomographic images on a display unit, and superimposing and displaying, as a first cross-section correction instruction region, a cross-section of a three-dimensional correction instruction region on the first tomographic image, which is used to correct a boundary of a region of interest extracted from the three-dimensional image, on the first tomographic image; and displaying at least one second tomographic image adjacent to the first tomographic image, which includes the three-dimensional correction instruction region, on the display unit, and superimposing and displaying, as a second cross-section correction instruction region, a cross-section of the three-dimensional correction instruction region on the second tomographic image, on the second tomographic image.

* * * * *